US007628828B2

(12) United States Patent
Bowen et al.

(10) Patent No.: US 7,628,828 B2
(45) Date of Patent: Dec. 8, 2009

(54) PROCESSOR FOR PRODUCING BIODIESEL FROM NATURAL FATS AND OILS

(75) Inventors: Galen M. Bowen, Chico, CA (US); Daniel P. Bowen, Chico, CA (US)

(73) Assignee: Springboard Biodiesel, LLC, Chico, CA (US)

( * ) Notice: Subject to any disclaimer, the term of this patent is extended or adjusted under 35 U.S.C. 154(b) by 347 days.

(21) Appl. No.: 11/520,509

(22) Filed: Sep. 12, 2006

(65) Prior Publication Data
US 2007/0056214 A1    Mar. 15, 2007

Related U.S. Application Data

(60) Provisional application No. 60/716,942, filed on Sep. 15, 2005.

(51) Int. Cl.
*C10L 1/18* (2006.01)
(52) U.S. Cl. .............................. 44/629; 44/437; 554/174
(58) Field of Classification Search .................. 44/437, 44/629; 544/174; 435/286.1
See application file for complete search history.

(56) References Cited

U.S. PATENT DOCUMENTS

| 3,445,341 | A  | * | 5/1969 | Liobis et. al. | ............. | 435/286.1 |
| 2005/0204612 | A1 | * | 9/2005 | Connemann et al. | ........... | 44/437 |
| 2006/0224005 | A1 | * | 10/2006 | Felly | .......................... | 554/174 |

* cited by examiner

*Primary Examiner*—Michael A Marcheschi
*Assistant Examiner*—Chantel Graham
(74) *Attorney, Agent, or Firm*—Beyer Law Group LLP (57) ABSTRACT

An integrated biodiesel processor is disclosed. The integrated biodiesel processor includes a main reaction tank for storing feedstock to be processed and within which the reactions take place to form a biodiesel product from the feedstock. The integrated biodiesel processor also includes one or more secondary tanks integrated with and disposed within the main reaction tank. The secondary tanks are configured to store reactionary ingredients to be released into the main reaction tank in order to generate reactions.

11 Claims, 6 Drawing Sheets

PROCESSOR FOR PRODUCING BIODIESEL FROM NATURAL FATS AND OILS

CROSS REFERENCE TO RELATED APPLICATIONS

This patent application claims the priority of U.S. Provisional Patent Application No. 60/716,942 entitled "PROCESSOR FOR PRODUCING BIODIESEL FROM NATURAL FATS AND OILS" filed Sep. 15, 2005, which is herein incorporated by reference.

BACKGROUND OF THE INVENTION

1. Field of the Invention

The present invention relates generally to biodiesel processors. More particularly, the present invention relates to biodiesel processors with integrated components.

2. Description of the Related Art

The process of making biodiesel from fats and oils of animal and vegetable origin (commonly referred to as feedstock) has been increasing in popularity in recent years. This is in part due to the shortage of world oil and the desire to make the world more green (e.g., recycle). In addition, rising fuel prices have motivated many consumers to seek a method of producing their own biodiesel at lower cost. Several attempts at creating machines for performing such processes have been made. Unfortunately, however, they typically consist of large systems with several external tanks and intricate piping systems connecting the tanks. As such, they tend to require fixed locations, are unwieldy and bulky, and are aesthetically unpleasing. Furthermore, because the systems utilize external piping and tanks, the systems can be very dirty to operate (e.g., leaks, etc.).

In view of the foregoing, there is a need for improved biodiesel processors, especially ones that are more compact, have a cleaner appearance, and that reduce the amount of external plumbing.

SUMMARY OF THE INVENTION

The invention relates, in one embodiment, to an integrated biodiesel processor. The integrated biodiesel processor includes a main reaction tank for storing materials to be processed and within which the reactions take place to form a biodiesel product. The integrated biodiesel processor also includes a secondary tank integrated with the main reaction tank. The secondary tank is configured to store a first set of reactionary ingredients to be released into the main reaction tank thereby causing a first reaction.

The invention relates, in one embodiment, to a biodiesel processor. The biodiesel processor includes a main reaction tank for storing materials to be processed and within which the reactions take place to form a biodiesel product. The biodiesel processor also includes a first internal tank integrated with and disposed inside the main reaction tank, and configured to store ingredients for an esterification reaction. The biodiesel processor further includes a second internal tank integrated with and disposed inside the main reaction tank, and configured to store ingredients for a transesterification reaction. The biodiesel processor additionally includes a motor configured to turn a shaft that has a stirring propeller on the end. The stirring propeller is located in the main reaction tank so as to mix ingredients stored in the main reaction tank. Moreover, the biodiesel processor includes various pumps as for example a first pump configured to move ingredients from the first internal tank into the main reaction tank; a second pump configured to move ingredients from the second internal tank into the main reaction tank; a third pump configured to move a washing agent into the main reaction tank; and a fourth pump configured to remove waste from the main reaction tank.

The invention relates, in one embodiment, to a method of producing biodiesel. The method includes storing oil comprised of triglycerides and free fatty acids inside a main reaction tank. The method also includes storing methanol inside a first tank internal to the main reaction tank. The method further includes storing methanol and a base catalyst inside a second tank internal to the main reaction tank. The method additionally includes reacting methanol stored in first tank with sulfuric acid and the oil stored in the main reaction tank to form methyl esters and triglycerides. The method further includes reacting methanol and sodium hydroxide stored in second tank with the methyl esters and triglycerides stored in main reaction tank to form glycerin, methyl esters and trace contaminants. Moreover, the method includes removing the glycerin from the main reaction tank thereby leaving fuel containing methyl esters and trace contaminants inside the main reaction tank and washing the fuel in order to remove the trace contaminants from the methyl esters thereby leaving a final biodiesel product.

BRIEF DESCRIPTION OF THE DRAWINGS

The invention will be readily understood by the following detailed description in conjunction with the accompanying drawings, wherein like reference numerals designate like structural elements, and in which.

DETAILED DESCRIPTION OF THE INVENTION

The invention is directed at a biodiesel processor used to make fatty acid alkyl esters (commonly known as biodiesel) from fats and oils of animal and vegetable origin (commonly referred to as feedstock.) This may be accomplished by one or more chemical processes including esterification and/or transesterification.

The main reaction tank on the invention may be filled with the oils to be processed. Secondary tanks, which may be integrated with the main reaction tank, may be filled with methyl or ethyl alcohol, or in some instances, another alcohol such as propyl alcohol, and lastly, catalysts may be added for the chemical reactions. These may include an acid such as sulfuric acid for the esterification, and a hydroxide or methoxide for the transesterification. Some of the most common transesterification catalysts used are sodium hydroxide or potassium hydroxide. Other catalysts for the transesterification could include various solid, non-consumable catalysts which are currently being developed in the industry.

Upon receiving the needed chemicals and oil to be processed, the processor will complete an esterification and/or transesterification reaction. This requires a means of mixing the chemicals such as a mechanical stirring device or a circulating pump. It may also require a premixing of a portion of the alcohol with the basic catalyst for use in a transesterification reaction. If an esterification and a transesterification are to be performed, then it may be beneficial to premix the alcohol and base catalyst while the esterification reaction is in progress in order to minimize time required.

Completion of the esterification and or transesterification reactions required to produce biodiesel will result in the production of glycerol alcohol as a waste product. This is removed from the biodiesel prior to usage of the fuel or washing of the fuel. A good method for removal of glycerol alcohol is simply allowing sufficient time for it to settle to the bottom of the reaction tank, as it is significantly heavier than biodiesel. Other methods, such as centrifugal separation, may be employed to accelerate the removal of glycerol alcohol.

Upon removal of glycerol alcohol from the biodiesel, the biodiesel is washed to remove any remaining trace amounts of glycerol alcohol, formed soaps, or reaction catalysts. Since these contaminants are generally quite hygroscopic, an effective means of their removal is to mix water with the biodiesel, and then allow the water to settle along with the contaminants. This water may then be pumped or drained out. It is often beneficial to repeat this process two or more times. Other methods may be used for removal of these contaminants such as an absorbent that can be mixed with the fuel, allowing it to attach itself to the trace contaminants contained in the fuel, or an absorbent contained in a porous vessel through which the biodiesel may be pumped to accomplish the removal of contaminants. If mixed with the biodiesel, the absorbent may then be removed by a process such as filtration or centrifugal separation. An example of an effective absorbent is magnesium silicate.

After the fuel is washed, if a water wash was used, there will likely still remain some water residue in the fuel. This must be removed prior to usage. A simple and effective way to accomplish this is through evaporation. Evaporation may be accelerated by applying heat to the fuel and stirring or agitating it to expose the fuel to the drier ambient air. Vacuum may also speed the evaporation process. After residual water is removed, the fuel is ready for use.

It should be noted that in order to meet government standards/requirements, in most circumstances, all of the glycerol alcohol, trace amounts of reaction catalysts, and water must be removed from the biodiesel before its use.

The above described process may be accomplished by the processor with varying levels of human interaction and instruction. In some embodiments, the processor may accomplish all of its tasks automatically, even going so far as to automatically fill itself from reservoirs of oil and reaction chemicals. In other embodiments, the processor may require instruction or interaction such as actuating valves and electrical switches for some or all steps of the process.

These and other embodiments of the invention are discussed below with reference to FIGS. 1-4. However, those skilled in the art will readily appreciate that the detailed description given herein with respect to these figures is for explanatory purposes as the invention extends beyond these limited embodiments.

Figure 1:
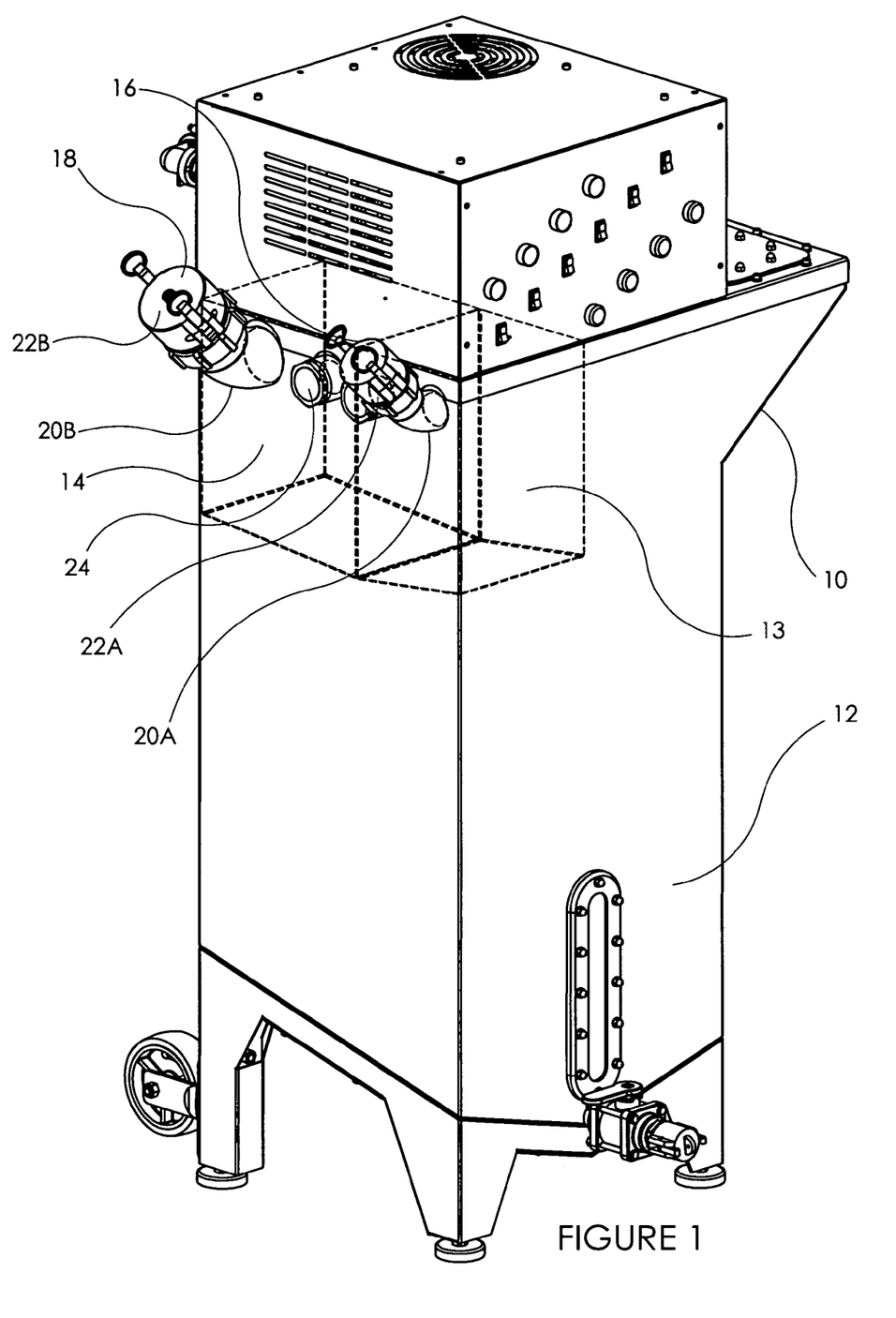
FIG. 1 is a perspective view of a biodiesel processor, in accordance with one embodiment of the present invention.
Figure 2:
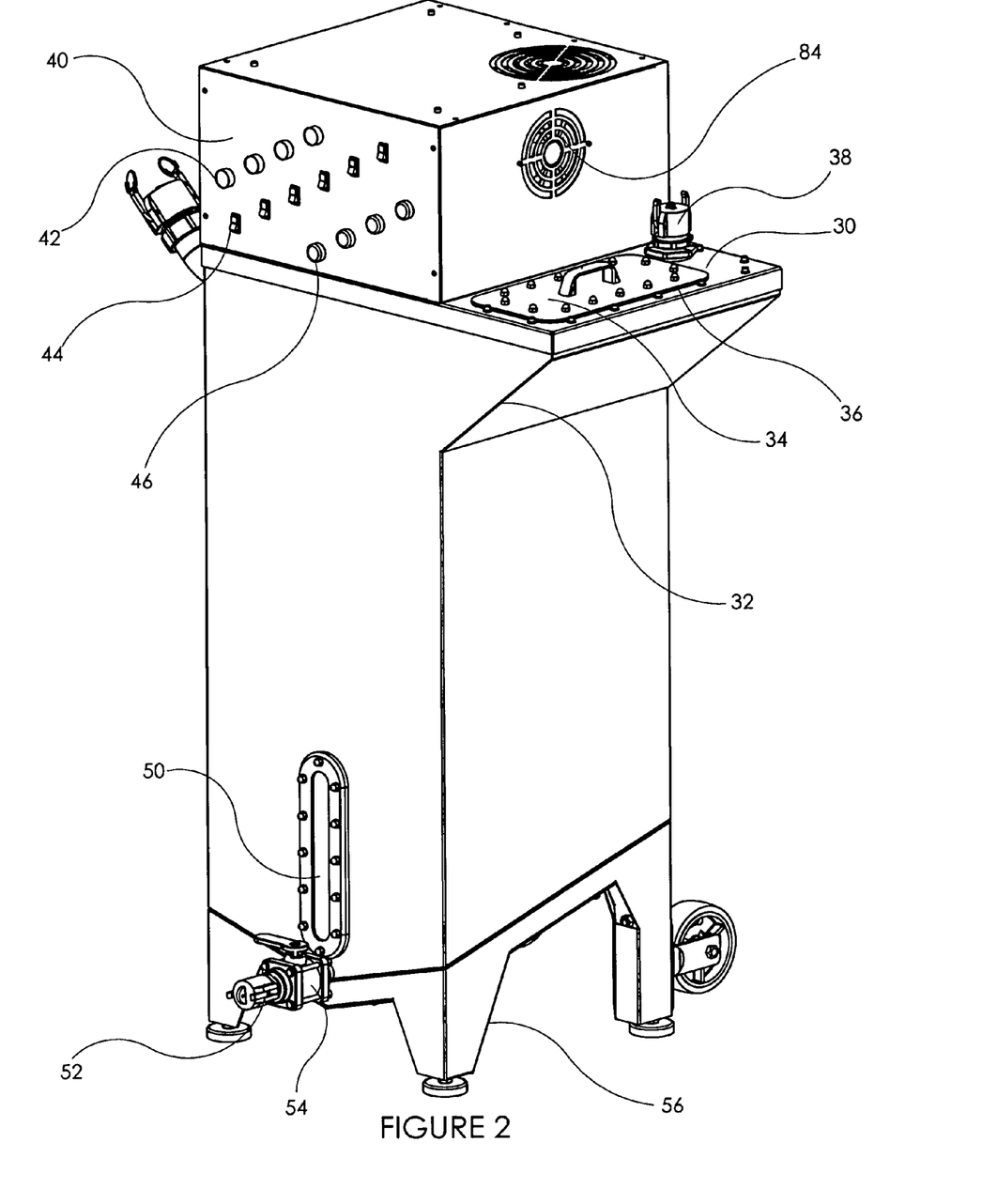
FIG. 2 is another perspective view of the biodiesel processor, in accordance with one embodiment of the present invention.
Figure 3:
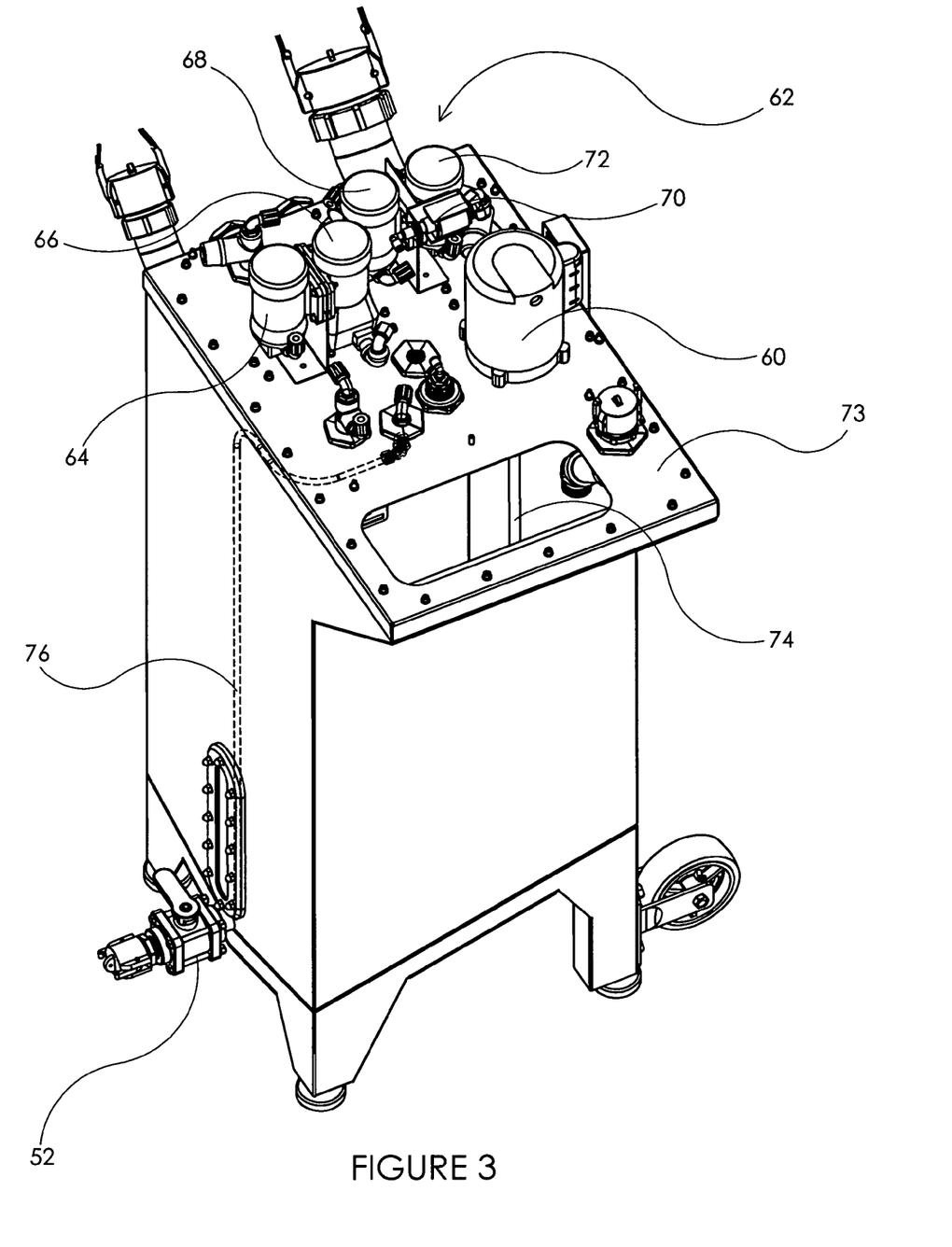
FIG. 3 is another perspective view of the biodiesel processor, in accordance with one embodiment of the present invention.

FIGS. 1-3 are various perspective views of a biodiesel processor 10, in accordance with one embodiment of the present invention. The biodiesel processor 10 has been optimized for factors such as compactness, reliability, ease of use, and manufacturability.

In one embodiment, the processor 10 is configured to perform an acid catalyzed esterification process followed by a base catalyzed transesterification process. This enables the use of grease and oils with high free fatty acid content with minimal saponification occurrence.

As shown in FIG. 1, the processor 10 includes a main reaction tank 12. The main reaction tank 12 is configured to contain the materials to be processed (e.g., triglycerides) and serve as the location for forming the biodiesel, i.e., where the reactions take place. The processor 10 also includes two secondary tanks 13 and 14 (shown with dashed lines). The secondary tank 13 is configured to contain ingredients to be used in esterification. By way of example, the secondary tank 13 may store alcohol. The secondary tank 14, on the other hand, is configured to contain ingredients to be used in transesterification. By way of example, secondary tank 14 may store alcohol and a base catalyst.

Although not shown in detail in FIG. 1, the secondary tanks 13 and 14 are fluidly coupled to the main reaction tank 12 so that fluids contained in the secondary tanks may be dispensed into the main reaction tank 12. Various coupling mechanisms including for example, valves, tubes, hoses, fittings, pipes, pumps, mass flow controllers, and the like, may be used. In one embodiment, the processor 10 separately connects each of the secondary tanks 13 and 14 to the main tank 12 via tubes and pumps. For example, each tank may include a tube having one end that projects down to the bottom of the tank, and an opposite end that couples to a suction port of a pump thereby allowing fluids contained therein to be pumped out into the main tank 12 or recirculated back into the secondary tanks.

In accordance with one embodiment, the secondary tanks 13 and 14 are integrated with the main tank 12 thereby creating a single unit. Furthermore, the secondary tanks 13 and 14 are stored internally within the main reaction tank 12. That is, the secondary tanks 13 and 14 are completely contained within the main tank 12. Integration of these three tanks allows for a more compact configuration, a cleaner appearance, and the absence of external plumbing. In the event of a plumbing failure, reactants would be contained within the machine, rather than spilling externally. Because it is contained internally, plumbing is also less susceptible to failure due to being hit, punctured, or jarred by an external force.

The position of the secondary tanks 13 and 14 within the main tank 12 may be widely varied. However, it is generally desirable to separate them from the mixing region of the main tank 12. In the illustrated embodiment, the secondary tanks 13 and 14 are positioned above the mixing region and more particularly at the top of the main tank 12. Furthermore, the tanks 13 and 14 are generally proximate one another to make filling easier. For example, the secondary tanks 13 and 14 may be located at the same side of the main tank 12 so that filling the tanks 13 and 14 can be performed at the same side of the processor 10.

In order to add ingredients to the secondary tanks 13 and 14, the secondary tank 13 includes an inlet 16 and the secondary tank 14 includes an inlet 18. The ingredients may be poured and/or pumped into the tanks 13 and 14 through the inlets 16 and 18. The inlets 16 and 18 may be embodied in a variety of ways. For example, any suitable opening, fitting or coupling may be used. In the illustrated embodiment, both of the inlets 16 and 18 include a pouring neck 20 so that fluids can be poured directly into the tanks 13 and 14 through the wall of the main tank 12. They also each include a cap 22 for closing off the opening of the pouring neck 20. For example, as shown, the inlet 16 includes a pouring neck 20A and a cap 22A and the inlet 18 includes a pouring neck 20B and a cap 22B. In one implementation, a "camlock" embodied cap is used on the inlets 16 and 18 to allow quick access and a positive seal.

In some cases, a sight glass 24 may be incorporated at each of the secondary tanks 13 and 14 to aid in achieving the correct volume of fluid (e.g., alcohol, base catalyst, etc.). In the event that greater automation is desired, the fill levels of the ingredients may be additionally or alternatively monitored by sensors such as float switches, conductivity sensors, proximity sensors, etc. These sensors could then control the pump or other device being used to fill the various compartments.

As shown in FIG. 2, the processor 10 further includes an inlet region 30 for dispensing materials directly into the main tank 12. The inlet region 30 may be embodied in a variety of ways. For example, any suitable opening, fitting or coupling may be used. In the illustrated embodiment, the inlet region 30 includes an angled pouring chute 32 that opens into the main tank 12. The inlet region 30 also includes a removable lid 34 that covers an opening 36 in the pouring chute 32. The opening 36 serves as the location where the oils to be processed can be poured, pumped, or, in the case of solidified fats, dumped. Alternatively, the lid 34 may be a door connected to the pouring chute 32. The inlet region 30 may also include an inlet pipe 38 that extends into the main tank 12. The inlet pipe 38 is configured to receive an acid catalyst and distribute the acid catalyst to the mixing region of the main tank 12 so that the acid catalyst does not directly come into contact with the walls of the main tank 12. This prevents corrosion caused by the acid directly contacting the walls of the main tank 12 before being diluted in the oil to be processed. This is also where the acid catalyst for the esterification reaction may be added. Like the pouring necks mentioned above, the inlet pipe 38 may include a removable cap.

The processor 10 may additionally include a user interface 40 for initiating one or more processing sequences associated with the processor 10. For example, once all ingredients have been supplied to the processor 10, the processor's control system (e.g., motors, pumps, etc.) may receive a command through the user interface 40 to begin the process. As should be appreciated, the process can take place automatically, without human intervention, by means of electronic controlling devices that are controlled by the user interface 40.

The user interface 40 may be widely varied. In the illustrated embodiment, the user interface 40 consists of buttons 42 that may be actuated by the user to command the electronic controller to start and stop the pre-programmed processes. There are also buttons to skip steps or reset the processes. Manual switches 44 are included as well, so that in the event of a controller failure, the machine may still be operated by means of manual inputs to these switches. Indicating lights 46 are present to alert the operator of the current progress of the processes. A label plate may be affixed to the panel which houses the buttons, lights, and switches, to inform the operator of the function of these devices. It should be appreciated, however, that this particular user interface is not a limitation and that other user interfaces may be used. For example, in some cases, a display may be desired to provide enhanced feedback to the operator. In addition, the display may include a transparent touch panel disposed thereon, and be configured to display a GUI that includes the controls mentioned above (or additional or alternative controls). A keyboard and standard input mechanisms may also be used.

The processor 10 may further include a viewing window 50 and an outlet 52 at the bottom of the main tank 12. The viewing window 50 allows a user to observe the settling of the waste glycerol alcohol upon completion of the chemical reactions. Alternatively or additionally, sensors may be used to monitor the process. The outlet 52, on the other hand, provides a means for dispensing the fluid contained within the main tank 12. Any suitable opening, coupling or fitting may be used. The outlet 52 typically includes a valve 54 for controlling the fluid therethrough. Upon observation of settled glycerin in viewing window 12, the glycerin can be drained off manually through outlet 52. The main reaction tank 12 may employ a sloped bottom to promote complete drainage. In the embodiment shown, reaction tank 12 has a bottom with a compounded slope, that is, the bottom surfaces slope, not only from the sides to the center, but also from the back to the front. Tanks 13 and 14 may also employ a sloped bottom surface to promote complete drainage into internal plumbing connected to the suction port of a pump.

The processor 10 may additionally include a base or stand 56 on which the main tank 12 rests. The stand 56 may include feet with leveling pads attached at the bottom. The stand 56 may also include a set of wheels attached to the feet so that the processor 10 can be easily moved.

FIG. 3 is a perspective view of the processor 10 with some of the component covers removed. As shown, the processor 10 includes a motor 60, various fittings 62, and pumps 64-72, which are all mounted on a top plate 73 that covers the top of the main tank 12.

The motor 60 is configured to turn a shaft 74, which has a stirring propeller on the end. The stirring propeller is submerged in the reacting chemicals stored the main reaction tank 12.

The fittings 62 provide a means for distributing pumped fluids through the top plate 73 and into the main tank 12. For the sake of clarity, the fluid carrying hoses between the pumps 64-72 and the fittings 62 as well as the hoses that extend into the main tank 12 from the fittings 62 have been removed.

The pumps 64-72 are configured to move fluids around the processor 10 during various stages of processing. Pump 64 is for example configured to pump the contents stored in tank 13 into the main reaction tank 12 to initiate the esterification stage. Pump 66 is configured to continuously circulated the contents of secondary tank 14 thereby dissolving the base catalyst stored therein. Alternatively or additionally, this may be accomplished by a mixing propeller and motor similar to those used to mix the fluid in main reaction tank 12. Pump 68, on the other hand, is configured to pump the contents stored in tank 14 into the main reaction tank 12 to initiate the transesterification stage. Furthermore, pump 70 is configured to pump wash water into the main tank 12 for the purpose of cleaning the fuel. By way of example, the water may be introduced into the main reaction tank 12 by pumping the water from an external vessel through an overhead spray nozzle and into the liquid contained in main reaction tank 12. Lastly, pump 72 is configured to pump out waste water and contaminants from the main tank 12 via suction tube 76.

In the embodiment shown, each transfer of liquid has its own dedicated pump, rather than using one pump along with valving to complete multiple transfers of liquid. This eliminates the risk of an actuated valve sticking, and also prevents any cross-contamination of fluids due to residual quantities of fluids left in the plumbing. However, in some cases, it may be desirable to reduce the number of pumps, and therefore multiple pumping operations may be performed a single pump with the appropriate valving. For example, a single pump in conjunction with the appropriate valving may be used to perform the pumping operations associated with pumps 64 and 68. Furthermore, in some cases, the pumps may be replaced partly or entirely by other control means such as gravity or pressure based systems.

Although not shown, the processor 10 may also include one or more heaters to heat fluids during reactions as wells as to help remove residual water from the fuel. The heaters may work in conjunction with one or more thermostats to keep the reactions at the optimal temperature. The heaters may be widely varied. In one embodiment, blanket heaters that surround the reaction vessel are used. By way of example, adhesive backed blanket heaters that adhere to the reaction vessel may be used.

A typical processing sequence in conjunction with the processor will now be described. The processing sequence may be manually controlled by using the buttons of the user interface or alternatively it may be automatically controlled using sensors and controllers. The processing sequence generally begins by pumping the contents contained in tank 13 into the main reaction tank 12 by pump 64 in order to initiate the esterification stage. During the esterification stage, the contents in tank 14 may be continuously circulated by pump 66 between the inlet and outlet ports of pump 66 in order to dissolve the base catalyst in tank 14 while the esterification is taking place. Thereafter, the contents contained in tank 14 may be pumped into the main tank 12 via pump 68 in order to initiate the transesterification stage.

Upon verifying that the reactions have occurred correctly, the fuel washing and drying cycles are initiated. For example, water may be pumped into the tank 12 from a separate water reservoir by means of pump 70. This water may be stirred in with the fuel for more thorough washing, and then be allowed to settle for a time. After settling, the waste water and contaminants may be removed and pumped into a separate waste container by pump 72. For example, the waste water and contaminants may be sucked up through suction tube 76, which projects down to the lowest point in main tank 12 and is plumbed to the suction port on pump 72. A level sensor such as one that uses conductivity to differentiate between fluids may be used to control the pump so as not to pump out any fuel with the waste water. That is, a sensor such as a conductivity sensor may instruct the pump 72 when to cease pumping out fluid. This wash cycle may take place one or more times.

Finally, in order to remove residual water from the fuel, the processor may apply heat and agitation through heaters and motor 60 and stirring propeller. This will accelerate the evaporation of residual water in the fuel. Alternatively or additionally, the fan 84, while serving its primary purpose of keeping internal electronic devices adequately cool, also serves to create a venturi effect, drawing water vapor out of inlet region 30. Upon completion of this step, the processor may actuate an indicator or alarm, such as a light, to inform the user that the biodiesel processing is complete. The biodiesel fuel may be gravity drained from outlet 52, or a device such as a fuel transfer pump may be attached to the outlet 52 in order to pump the biodiesel into another container.

It may be advantageous to require human intervention before beginning to wash the fuel, as this allows the user to ensure that the reactions have occurred correctly. If they have not, simple steps can be taken to save the batch. Attempts to save a batch which has not reacted correctly will have a higher probability of success if the fuel has not been washed with water yet, as water is a contaminant for esterification and transesterification reactions. If a greater level of automation is desired, the human interaction at this point may be eliminated by the use of a sensor, such as a conductivity sensor.

Referring to FIGS. 1-3, the size of the tanks may be widely varied. The size typically varies according to the specific needs of the processor. In one embodiment, in order to make a compact unit, the processor is configured to process up to 50 gallons of feedstock per batch. In order to process this amount, the main tank is configured with about 80 internal gallons of space of which at least 10 gallons of volume are partitioned off for the secondary tanks disposed internally therein. For example, the first secondary tank 13 may be configured to hold at least 4 gallons, and the second secondary tank 14 may be configured to hold at least 6 gallons thereby leaving up to 70 gallons of space for the main tank 12.

The remaining 70 gallons of space provide enough room for the feedstock and the addition of processing fluids, the volume of which fluctuates throughout processing. For example, during the esterification and transesterification stages, the volume of fluid inside the main tank consists of about 10 gallons of fluid from the secondary tanks and about 50 gallons of fluid from the feedstock. However, this is typically drained back down to 50 gallons. The fluids added during washing may bring this number close to 70 gallons, but this too is drained out of the main tank before the maximum volume is reached.

In one example, for this volume, approximately 10 gallons of alcohol, 1520 grams of sodium hydroxide or 2128 grams of potassium hydroxide, and 190 milliliters of sulfuric acid may be used in the process. Six of these gallons of alcohol are mixed with the base catalyst (sodium or potassium hydroxide) and contained in tank 14. Four of these gallons of alcohol are contained in tank 13.

Furthermore, the various components of the processor may be formed from a variety of materials including but not limited to plastics, metals and the like. In one embodiment, the main reaction tank 12, as well as secondary tanks 13 and 14, are formed from stainless steel sheet. Stainless steel has the corrosion resistant properties needed to prevent degradation of the reaction vessels. One stainless alloy that is well suited for use in the construction of the processor is stainless steel 304, as it has a good balance of corrosion resistance, weldability, and formability. These are important properties as the tanks are generally formed into the desired shape and then welded along the seams to prevent any fluid leakage. When the proper gage of stainless steel sheet is used, it can function dually as the containment vessel for the fluids involved and also as the main structural component of the processor, eliminating the need for any sort of structural frame. In one implementation, the stainless steel sheet used to form the tanks has gage between about 10 and about 18, and more particularly about 14.

In one embodiment, all of the stainless steel sheet components including the main tanks as well as secondary tanks may be cut from one 6'×12' sheet of stainless steel. This is very advantageous for reducing cost and complexity in manufacturing. Especially when production quantities are relatively low, only using one sheet of material per processor will greatly reduce waste of a relatively expensive material.

In one embodiment, the processor is compact to the extent that it could fit into a rectangular prism of a volume of less than 1 cubic foot per gallon of batch processing capability, i.e. the 50 gallon processor as described above has overall dimensions such that it could fit in a box of less than 50 cubic feet.

Figure 4:
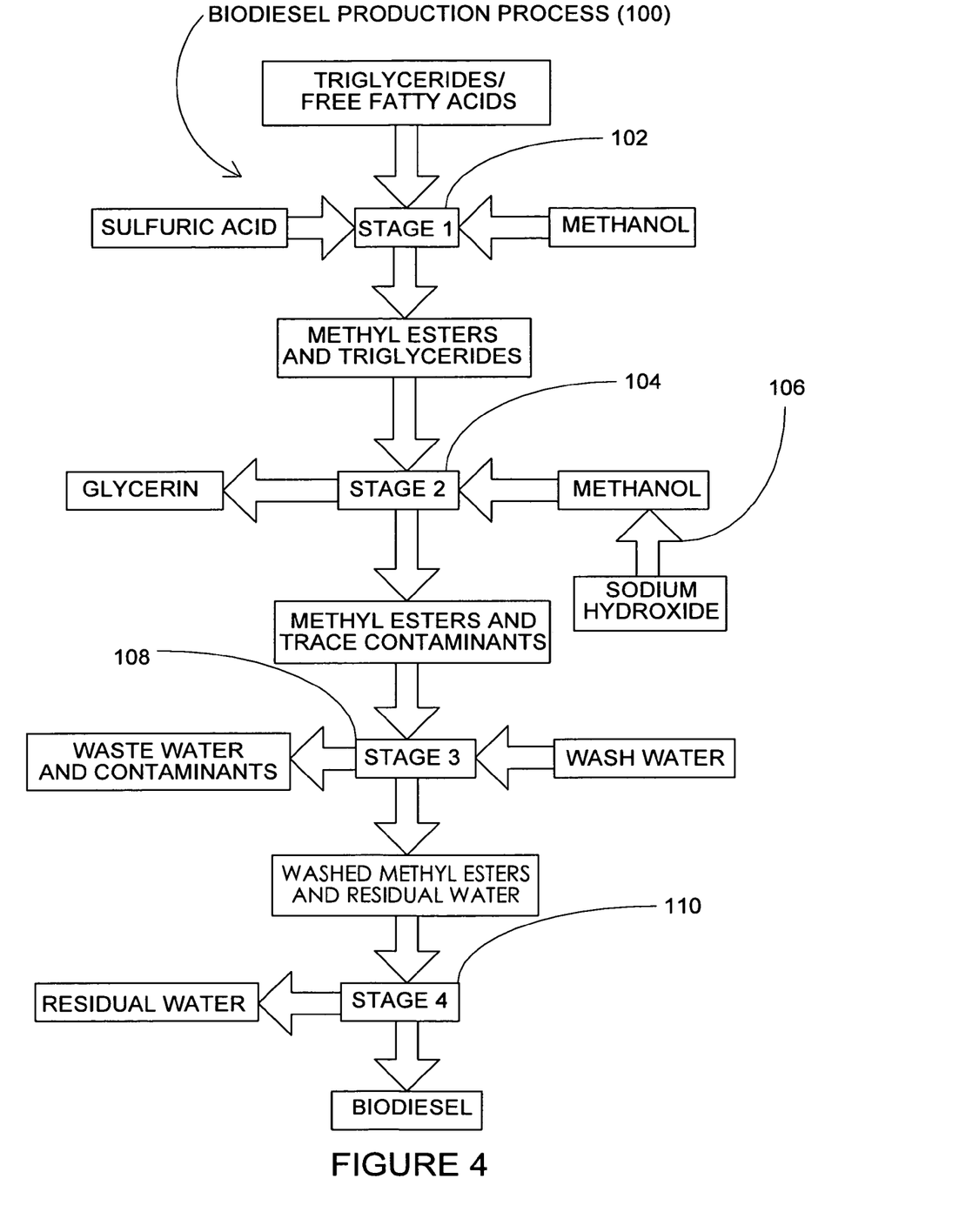
FIG. 4 depicts an exemplary flow diagram describing a process for producing biodiesel, in accordance with one embodiment of the present invention.

FIG. 4 depicts an exemplary flow diagram describing a process (100) for producing biodiesel, in accordance with one embodiment of the present invention. The process may for example be performed by the processor depicted in FIGS. 1-3. The process (100) generally uses an acid catalyzed esterification followed by a base catalyzed transesterification. In this example, sulfuric acid is shown as the acid catalyst, sodium hydroxide is shown as the base catalyst, and methyl alcohol is the alcohol used. It should be noted, however, that these ingredients are not a limitation, and that other ingredients may be used in their place.

As shown, the process 100 consists of several stages. In stage 1 (102), oil comprised of triglycerides and free fatty acids (feedstock), sulfuric acid, and methanol are reacted to form methyl esters and triglycerides, (along with a predictable, minimal level of free fatty acids). This may, for example, be accomplished in the processor described above. By way of example, the feedstock along with sulfuric acid may be placed in the main reaction tank 12. Furthermore, methanol may be placed in the secondary tank 13 and methanol and sodium hydroxide may be placed in secondary tank 14. Once the processor's controller receives the command to begin the process, the methanol contained in tank 13 may be pumped into the main reaction tank 12 via pump 64, thereby instigating the esterification reaction. At the same time, the methanol and sodium hydroxide mixing commences in reaction tank 14 (106) by means of mixing pump 66.

In stage 2 (104), methanol and sodium hydroxide are added to the methyl esters and triglycerides by means of pump 68. This leaves methyl esters, glycerin, and trace contaminants. The glycerin is removed, thereby leaving the methyl esters and trace contaminants. This may, for example, be accomplished in the processor described above. The glycerin may be removed by manual drainage through outlet 52.

In stage 3 (108), wash water is added to the methyl esters and trace contaminants in order to remove the contaminants from the methyl esters. The waste water and contaminants are removed thereby leaving the methyl ester and residual water. This may, for example, be accomplished in the processor described above. By way of example, the water may be introduced into the main reaction tank 12 by pumping the water from an external vessel with pump 70, through an overhead spray nozzle and into the liquid contained in main reaction tank 12. The waste water and contaminants are allowed to settle, then are drawn through suction tube 76 and pumped out by pump 72. A sensor such as a conductivity sensor may instruct the pump 72 when to cease pumping out fluid. In one embodiment, the fuel is washed three times. During the second and third washes, the fuel and wash water are agitated together by mixing motor 60 to more thoroughly remove any hygroscopic contaminants. This agitation is not performed during the initial wash. Before the initial wash, levels of residual base catalyst may be so high as to produce an undesirable saponification reaction if the unwashed biodiesel and water are agitated together. After the initial wash, agitation of the biodiesel with the wash water does not present a threat of excessive saponification. In the embodiment shown, approximately 15 gallons of water are used per wash cycle.

In stage 4 (110), the residual water is removed, thereby leaving biodiesel. This may, for example, be accomplished in the processor described above. By way of example, the water may be removed from the main reaction tank 12 by heating the methyl esters and agitating them with motor 60 while lid 34 is removed to encourage evaporation of residual water. Fan 84 (as shown in FIG. 2), while serving its primary purpose of keeping internal electronic devices adequately cool, also serves to create a venturi effect, drawing water vapor out of inlet region 30.

Figure 5:
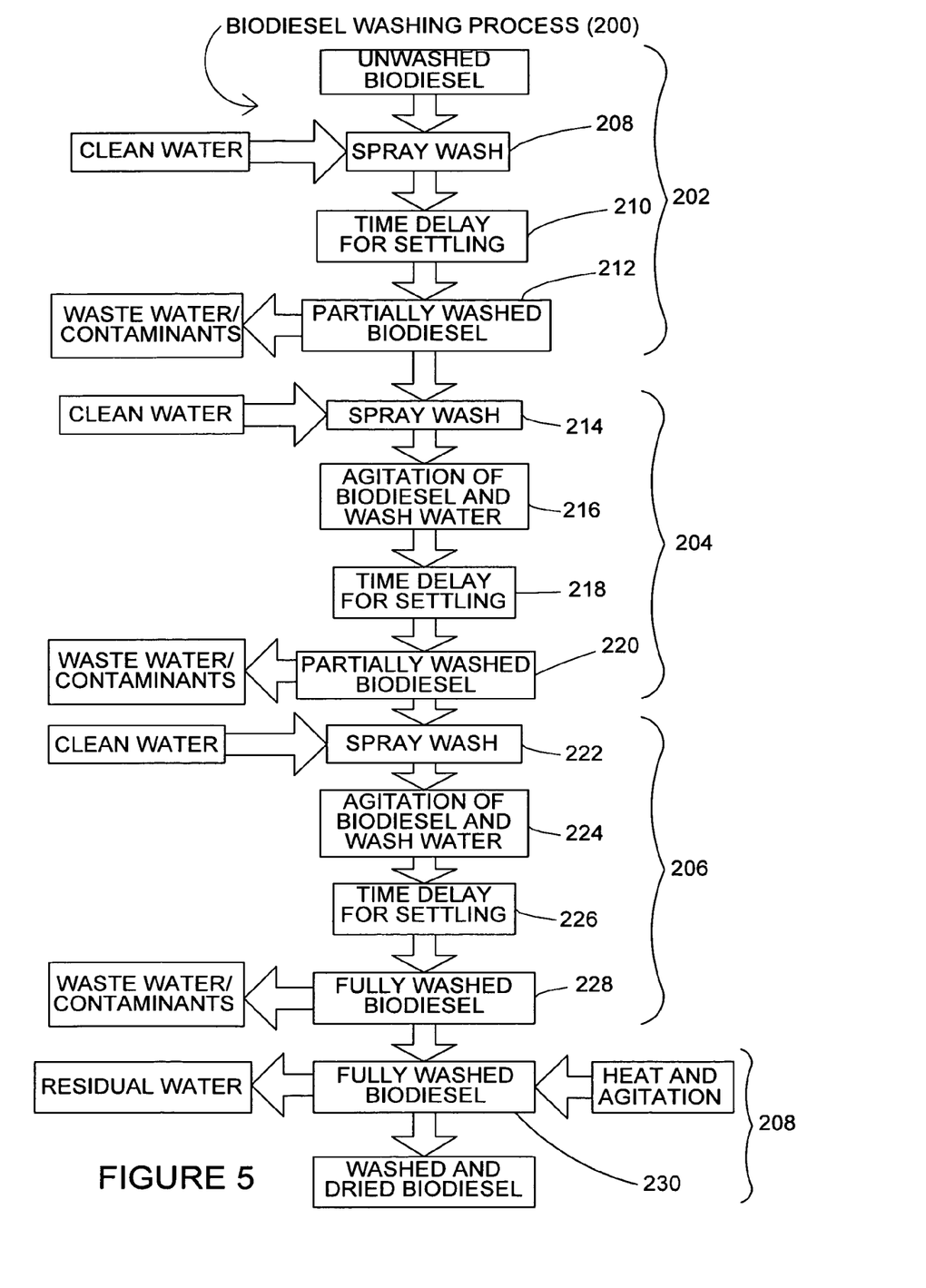
FIG. 5 is a flow diagram showing a method of washing a fuel, in accordance with one embodiment of the present invention.

FIG. 5 is a flow diagram showing a method 200 of washing a fuel, in accordance with one embodiment of the present invention. The method 200 may for example be performed in stage 3 (108) described in FIG. 4. The method 200 generally includes four washing steps 202-208. The first washing step 202 includes blocks 209-212. In block 209, water is introduced into the main reaction tank as an initial wash. Thereafter, in block 210, the wash water is allowed to settle so that the wash water separates from the fuel. The wash water forms waste water by collecting trace contaminants found in the fuel. Following block 210, the method proceeds to block 212 where waste water is removed from the main reaction tank. The second washing step 204 includes blocks 214-220. In block 214, water is introduced into the main reaction tank as a secondary wash. Thereafter, in block 216, the water and fuel are agitated to form a homogenous mixture. In block 218, the wash water is allowed to settle so that the wash water separates from the fuel. Following block 218, the second wash proceeds to block 220 where waste water is removed from the main reaction tank. The third washing step includes blocks 222-228. In block 222, water is introduced into the main reaction tank as a third wash. Thereafter in block 224, the water and fuel are agitated to form a homogenous mixture. In block 226, the wash water is allowed to settle so that the wash water separates from the fuel. Following block 226, the second wash proceeds to block 228 where waste water is removed from the main reaction tank. Following the three washing steps 202-206, the method may include an additional block 230 where the fuel is dried to remove residual moisture from the fuel. This may for example be accomplished by agitating and heating the fuel with the stirrer and heaters. Alternatively of additionally, the fuel may be dried by utilizing a fan to promote water evaporation.

In one example, after performing reactions on 50 gallons of feedstock with 10 gallons of reactionary fluids, and removing the glycerin from the resultant product, the step of introducing water includes spraying between about 10 and about 20 gallons of water into the fuel and the step of settling includes allowing the wash water to settle for 2 to 3 hours before being pumped out. Furthermore, the step of removing the waste water includes automatically pumping out fluid until conductivity sensor at the bottom of main reaction tank senses biodiesel rather than water.

Figure 6:
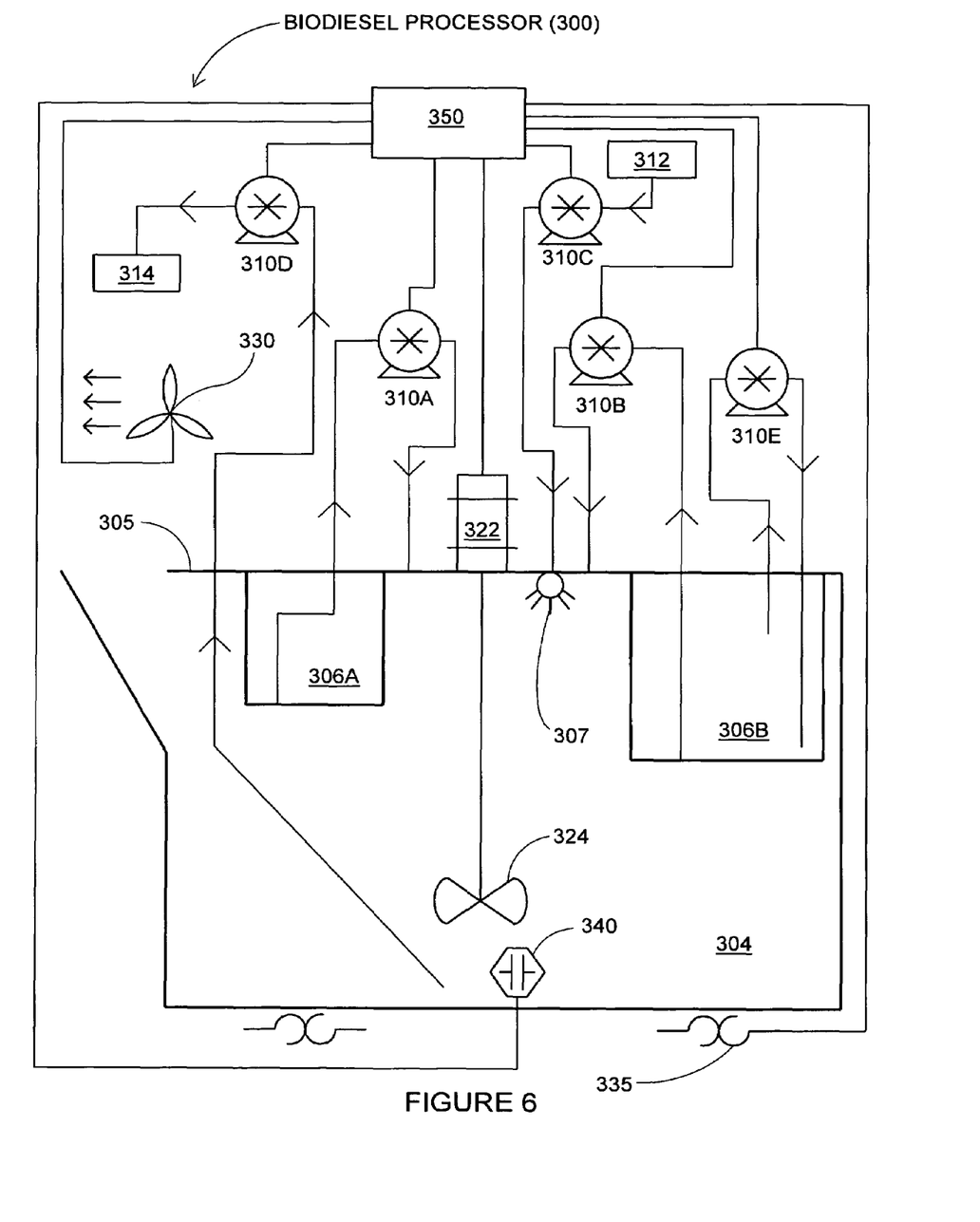
FIG. 6 is a simplified block diagram of a biodiesel processor, in accordance with one embodiment of the present invention.

FIG. 6 is a simplified block diagram of a biodiesel processor 300, in accordance with one embodiment of the present invention. The biodiesel processor 300 is configured transform feedstock into a biodiesel product. The biodiesel product may for example be used to fuel vehicles, generators, heaters, or any other devices which burn diesel fuel or fuel oil.

As shown, the biodiesel processor 300 includes a tank system 302 comprising a main reaction tank 304 and one or more secondary tanks 306. The main reaction tank 304 is configured to store the feedstock to be processed and provide an enclosure within which the reactions take place to form the biodiesel product. The secondary tanks 306 on the other hand are configured to store reactionary ingredients to be released into the main reaction tank 304 thereby causing reactions that help create the biodiesel product. The secondary tanks 306 are configured to be isolated from each other and the main reaction tank 304, i.e., no cross contamination of material stored therein. The number of secondary tanks 306 may be based on the number of reactions required to transform the feedstock into the biodiesel product. In one embodiment, two reactions are required. For example, an esterification reaction followed by a transesterification reaction. Therefore, the tank system 302 generally includes a first secondary tank 306A for holding ingredients for an esterification reaction and a second secondary tank 306B for holding ingredients for an transesterification reaction.

In accordance with one embodiment, the secondary tanks 306 are integrated with the main reaction tank 304 thereby creating a single tank unit, which makes the biodiesel processor 300 more compact and aesthetically pleasing. Furthermore, the secondary tanks 306 are disposed inside the main reaction tank 304, which makes plumbing easier and creates a uniform looking system.

The biodiesel processor 300 also includes a pumping arrangement for transferring fluids between the various tanks 304 and 306 as well as into and out of the biodiesel processor 300. The pumping arrangement generally includes one or more pumps 310. In most cases, each fluid transfer includes its own pump, however, in some cases valving systems can be used to reduce the number of pumps. In the illustrated embodiment, the pumping arrangement includes pumps 310A-310E.

A first pump 310A is configured to deliver the reactionary ingredients from the first secondary tank 306A to the main reaction tank 304. The first pump 310 A may for example be disposed between various hoses or tubes or fittings that couple the first secondary tank 306A to the main reaction tank 304. During operation, the first pump 310A sucks the reactionary ingredients from the first secondary tank 306A and dispenses them into the main reaction tank 304 through fittings or internal tubes or hoses. Once discharged from the fittings or internal tubes or hoses, the ingredients begin to react with the feedstock stored in the main reaction tank 304.

A second pump 310B is configured to deliver the reactionary ingredients from the second secondary tank 306B to the main reaction tank 304. The second pump 310B may for example be disposed between various hoses or tubes or fittings that couple the second secondary tank 306B to the main reaction tank 304. During operation, the second pump 310B sucks the reactionary ingredients from the second secondary tank 306B and dispenses them into the main reaction tank 304 through fittings or internal tubes or hoses. Once discharged from the fittings or internal tubes or hoses, the ingredients begin to react with the feedstock stored in the main reaction tank 304.

A third pump 310C is configured to deliver a washing agent such as water from a washing agent tank 312 to the main reaction tank 304. The third pump 310C may, for example, be disposed between various hoses or tubes or fittings that couple the washing agent tank 312 to the main reaction tank 304. During operation, the third pump 310C sucks the reactionary ingredients from the washing agent tank 312 and dispenses them into the main reaction tank 304 through nozzle 307 that is mounted on the underside of top plate 305, allowing the water to be spayed down on top of the fuel to be washed. Once discharged from the fittings or internal tubes or hoses, the ingredients begin to mix with the unwashed fuel stored in the main reaction tank 304. Alternatively, the washing agent may be distributed via a valve and a water agent source. By way of example, the washing agent source may be an external water supply.

A fourth pump 310D is configured to remove waste fluids from the main reaction tank 304 and deliver them to a waste fluid tank 314. The fourth pump 310D may for example be disposed between various hoses or tubes or fittings that couple the main reaction tank 304 to the waste fluid tank 314. During operation, the fourth pump 310 sucks the waste fluid from the main reaction tank 304 and dispenses them into the waste fluid tank or drain 314.

Additional pumps may be provided to promote mixing. For example, recirculatory pumps may be used in any of the tanks to move fluid in and out of the tank such that the ingredients stored therein are mixed. In the illustrated embodiment, a fifth pump 310E is configured to recirculate the ingredients stored in the second secondary tank 306B. The fifth pump 310E may, for example, be disposed between various hoses or tubes or fittings that start and end at the second secondary tank 306B.

During operation, the fifth pump 310E sucks the fluid from the second secondary tank 306B and reintroduces it back into the second secondary tank 306B.

In accordance with one embodiment, the pump arrangement includes fittings and hoses and tubes that are all disposed above a top plate 305 of the main reaction tank 304 underneath a cover thereby keeping them internal to the processor (e.g., not exposed and hidden from view).

The biodiesel processor 300 also includes a mixing/agitator assembly. The mixing agitator assembly 320 includes a motor 322 with a shaft that spins a stirring blade 324 inside the main reaction tank 304, positioned roughly near the halfway point in the depth of the fluid, in order to mix ingredients as well as to agitate them.

The biodiesel processor 300 may also include one or more fans 330 for promoting evaporation of the fluid contained inside the main reaction tank 304.

The biodiesel processor 300 may also include one or more heaters 335 for heating the contents contained within the main reaction tank.

The biodiesel processor 300 may also include a conductivity sensor 340 disposed at the outlet of the main reaction tank 304. The conductivity sensor 340 is configured to sense the conductivity of the fluid exiting the main reaction tank 304 so as to determine whether the fluid is waste water or biodiesel product. If the conductivity indicates biodiesel product then a signal is sent to the fourth pump 310D to shut off. If the conductivity indicates waste water, then a signal is sent to the fourth pump 310D to maintain pumping action.

The biodiesel processor 300 may also include a controller 350 for controlling the various components of the biodiesel processor 300. For example, the controller 350 may include capabilities for, but not limited to, controlling the pumping action of the pumps 310 to initiate reactions or wash the fuel, controlling the stirring action of the motor 322 so as to mix or agitate the fluid contained in the main reaction tank 304, controlling the fan 330 to promote evaporation, controlling the heaters 335, etc. The controller 350 may also be configured to monitor sensors such as the conductivity sensor 340. Furthermore, the controller 340 may be arranged to act as both an operator console and master controller of the system. That is, all system interfaces with an operator and the user's facilities may be made through the controller. Commands may be issued to and status may be monitored from all components so as to facilitate completion of assigned tasks.

In one embodiment, the controller 350 is programmable configured to initiate an automated biodiesel transformation sequence. By being programmable different sequences may be utilized depending on various factors including but not limited to the amount of material to be processed, the type of material used in the process, etc.

During a typical sequence, the controller 350 may cause the first pump 310A to turn on in order to initiate a first reaction, and turn off when the first secondary tank 306A is empty or once the desired amount has been dispensed. The controller 350 may also cause the fifth pump 310E to recirculate the ingredients in the second secondary tank 306B to promote mixing. This may be done when the first pump 310A is pumping and subsequently when the first reaction is taking place. The controller 350 may additionally cause the second pump 310B to turn on in order to initiate a second reaction, and turn off when the second secondary tank 306B is empty or once the desired amount has been dispensed. This step may be initiated by a sensor that indicates when the first reaction is complete, or it may be initiated at a predetermined time after the first pumping action. For example, the first pump 310A may activate at T1 and the second pump 310B may activate at T2.

The controller 350 may further cause the third pump 310C. to turn on in order to initiate washing and turn off when a predetermined volume of washing fluid has been added to or reached within the main reaction tank 304. This step may be initiated by a sensor that indicates when the second reaction is complete, or it may be initiated at a predetermined time after the first pumping action. For example at T3. Moreover, the controller 350 may cause the fourth pump 310D to turn on in order to remove waste fluid from the main reaction tank 304 and turn off when substantially all of the waste fluid has been removed. By way of example, the fourth pump 310D may turn on at T4 after the wash fluid has settled, and turn off when the conductivity sensor 340 indicates biodiesel product is being released. The washing steps may be repeated as needed to remove contaminants.

The controller 350 may also cause the motor 320 to turn on when mixing, agitation or drying is needed. The controller 350 may further cause the heaters 335 to heat the main reaction tank or other tanks as needed during reactions and/or during washing and drying. The controller 350 may additionally cause the fan 330 to turn on when residual moisture needs to be removed as for example at the end of the processing sequence.

A typical style of pump 310 A-E that may be employed, by way of example and not by way of limitation, is a diaphragm pump, which effectively isolates the fluid being transferred from the driving mechanism, a feature of importance when pumping chemicals like those used in biodiesel processing. These pumps are by no means the only style that may be employed, as there are several others that may accomplish their tasks satisfactorily, though the cost and complexity of plumbing may vary with each style.

A typical stirring motor 322 which may be employed, by way of example and not by way of limitation, is an AC induction motor, with a C-face mounting configuration, allowing it to be bolted directly to the top side of top plate 305, with the shaft projecting downward into the main reaction tank 304.

A typical controller 350 which may be used, by way of example and not by way of limitation, is a programmable logic controller, which allows a customized sequence to be written to the controller's memory without the significant cost of building a custom chip. If large numbers of the processors are to be produced, it may be more cost effective to use a custom manufactured chip to serve the role of the controller 350, rather than a programmable logic controller. These are not the only types of controllers that may be used, as the controller function could even be accomplished by a combination of electro-mechanical timers and relays.

While this invention has been described in terms of several preferred embodiments, there are alterations, permutations, and equivalents, which fall within the scope of this invention. It should also be noted that there are many alternative ways of implementing the methods and apparatuses of the present invention. It is therefore intended that the following appended claims be interpreted as including all such alterations, permutations, and equivalents as fall within the true spirit and scope of the present invention.

What is claimed is:

1. An integrated biodiesel processor, comprising:
    a main reaction tank for storing materials to be processed, the main reaction tank having a reaction chamber;
    plumbing coupled with the main reaction tank, the plumbing being unexposed and disposed within the main reaction tank, thereby helping to reduce risk of external spillage of fluids from the plumbing and protect the plumbing from damages;
    a first secondary tank disposed within the main reaction tank, and configured to store a first set of reactionary ingredients to be released into the reaction chamber of the main reaction tank thereby causing an esterification reaction in the reaction chamber, the first secondary tank including a port configured to allow passage of the first set of reactionary ingredients into the reaction chamber by way of the plumbing;
    a second secondary tank disposed within the main reaction tank, and configured to store a second set of reactionary ingredients to be released into the reaction chamber of the main reaction tank thereby causing a transesterification reaction in the reaction chamber, the biodiesel processor configured such that both the esterification and transesterification reactions occur in the same reaction chamber to produce biodiesel in the reaction chamber, the second secondary tank including a port configured to allow passage of the second set of reactionary ingredients into the reaction chamber by way of the plumbing;
    wherein the biodiesel processor fits into a rectangular prism having a volume of less than 1 cubic foot per gallon of batch processing capability.

2. The integrated biodiesel processor as recited in claim 1 wherein the ingredients for transesterification are pre-mixed within the second secondary tank.

3. The integrated biodiesel processor as recited in claim 1 wherein the first secondary tank is configured to hold ingredients for an esterification reaction, and wherein the second secondary tank is configured to hold ingredients for a transesterification reaction.

4. The integrated biodiesel processor as recited in claim 3 further comprising:
    a viewing window located in a lower portion of the main reaction tank, the viewing window allowing an operator to view the separation of biodiesel from a glycerol alcohol bi-product after a transesterification reaction.

5. The integrated biodiesel processor as recited in claim 1 further comprising:
    a pumping arrangement configured to independently transfer contents of the first and second secondary tanks to the reaction chamber, the pumping arrangement including a first pump and a second pump configured to transfer contents of the first secondary tank and the second secondary tank to the reaction chamber, respectively.

6. The biodiesel processor as recited in claim 5 further comprising:
    a programmable electronic controller employed to control various operations of the biodiesel processor including at least the mixing of ingredients in the main reaction tank and the fluid transfer necessary to carry out the processes that result in a biodiesel product.

7. The biodiesel processor as recited in claim 5 further comprising an electrical conductivity sensor located at the bottom of the main reaction vessel, the electrical conductivity sensor being capable of differentiating between wash water and biodiesel, thereby allowing automated waste water removal during a fuel washing process.

8. The biodiesel processor as recited in claim 5 further comprising:
    a fan configured to increase the rate of evaporation of water from biodiesel that is being dried.

9. The biodiesel processor as recited in claim 5 further comprising:
   a heater configured to heat the contents stored in the main reaction tank.

10. The biodiesel processor as recited in claim 5 further comprising:
    a fifth pump configured to recirculate the ingredients held in the second internal tank thereby promoting mixing of the ingredients within the second internal tank.

11. A biodiesel processor, comprising:
    a reaction chamber;
    plumbing coupled with the reaction chamber;
    a plurality of storage chambers coupled with the reaction chamber, each storage chamber configured to deliver ingredients into the reaction chamber the plurality of storage chambers including a first storage chamber and a second storage chamber, the first storage chamber configured to store ingredients for an esterification reaction, the second storage chamber configured to store ingredients for a transesterification reaction, the first storage chamber including a port configured to allow passage of the ingredients for the esterification reaction into the reaction chamber by way of the plumbing, the second storage chamber including a port configured to allow passage of the ingredients for the esterification reaction into the reaction chamber by way of the plumbing;
    a motor configured to turn a shaft that has a stirring propeller on the end, the stirring propeller being located in the reaction chamber so as to mix ingredients stored in the reaction chamber;
    a first pump configured to move ingredients from the first storage chamber into the reaction chamber via the plumbing, thereby facilitating an esterification reaction within the reaction chamber;
    a second pump configured to move ingredients from the second storage chamber into the reaction chamber via the plumbing, thereby facilitating a transesterification reaction within the reaction chamber;
    a third pump configured to move a washing agent into the reaction chamber;
    a fourth pump configured to remove waste from the reaction chamber; at least one peripheral device, each peripheral device being one of a group consisting of: a programmable electronic controller, a fan, a wheel, an electrical conductivity sensor, a heater, a pump, a fitting, a tube, a motor, a window, a sensor, an electrical system and a control panel; and
    a housing made of sheet metal, the housing substantially encasing at least the reaction chamber, the plurality of storage chambers, the plumbing coupling the plurality of storage chambers with the reaction chamber, the motor, the first pump, the second pump, the third pump and the fourth pump, thereby helping to make the biodiesel processor more compact, reduce risk of external spillage of fluids from the plumbing and improve the portability and reliability of the biodiesel processor, wherein the biodiesel processor fits into a rectangular prism having a volume of less than 1 cubic foot per gallon of batch processing capability.

* * * * *

UNITED STATES PATENT AND TRADEMARK OFFICE
CERTIFICATE OF CORRECTION

PATENT NO. : 7,628,828 B2
APPLICATION NO. : 11/520509
DATED : December 8, 2009
INVENTOR(S) : Bowen et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 434 days.

Signed and Sealed this

Second Day of November, 2010

David J. Kappos
*Director of the United States Patent and Trademark Office*